United States Patent [19]

Arias-Alvarez

[11] Patent Number: 4,532,131
[45] Date of Patent: * Jul. 30, 1985

[54] THERAPEUTIC COMPOSITIONS

[75] Inventor: Antonio J. Arias-Alvarez, Carpatos, Mexico

[73] Assignee: T and R Chemicals, Inc., Clint, Tex.

[*] Notice: The portion of the term of this patent subsequent to Apr. 27, 1999 has been disclaimed.

[21] Appl. No.: 630,202

[22] Filed: Jul. 12, 1984

Related U.S. Application Data

[60] Division of Ser. No. 608,122, May 8, 1984, , which is a continuation-in-part of Ser. No. 498,488, May 28, 1983, Pat. No. 4,464,357, and Ser. No. 498,489, May 26, 1983, Pat. No. 4,462,988.

[51] Int. Cl.³ .............................................. A61K 33/04
[52] U.S. Cl. ..................................................... 424/162
[58] Field of Search ......................................... 424/162

[56] References Cited

U.S. PATENT DOCUMENTS 4,327,083  4/1982  Alvarez ............................. 424/162

Primary Examiner—Stanley J. Friedman

[57] ABSTRACT

Sodium bisulfite is used to treat epilepsy.

7 Claims, No Drawings

THERAPEUTIC COMPOSITIONS

CROSS REFERENCE TO RELATED APPLICATION

This application is a division of Ser. No. 608,122, filed May 8, 1984, which is a continuation-in-part of both Ser. No. 498,488, filed May 26, 1983, now U.S. Pat. No. 4,464,357 and Ser. No. 498,489, filed May 26, 1983, now U.S. Pat. No. 4,462,988.

BACKGROUND OF THE INVENTION

Sodium bisulfite (usually shown by formula to be NaHSO$_3$) has heretofore been used for many commercial purposes, as a preservative for prevention of the deterioration of liquids, such as food stuffs and pharmaceutical solids and solutions, and has been used medically externally for parasitic skin diseases and internally as a gastrointesinal antiseptic.

The sodium bisulfite of commerce consists chiefly of sodium metabisulfite, Na$_2$S$_2$O$_5$, and for purposes of this invention such is believed to possess the same properties as (and to be equivalent to) the true sodium bisulfite when dissolved in an aqueous solution.

The use of sodium bisulfite and metabisulfite in the treatment of hypertension is described in my U.S. Pat. No. 4,327,083 and is also described as an antithrombotic agent useful for prolonging both prothrombin time (PT) and partial thromboplastin time (PTT) of blood or blood plasma in my U.S. Pat. No. 4,401,654.

BRIEF SUMMARY OF THE INVENTION

In a first aspect of my invention I have discovered that sodium bisulfite, either as such or in an aqueous solution of sulfite ions (SO$_3$=), is useful in low doses and over extended periods in the treatment of the symptoms of arthritis and arthritic conditions when administered to humans in an aqueous dilute solution.

Treatment of Arthritis: A first embodiment of the present invention is directed to the treatment of arthritis and symptoms experienced by those afflicted with arthritic conditions. The most common form of arthritis is rheumatoid arthritis which is characterized by a chronic inflammatory condition affecting particularly the small joints of the hands and feet, although the larger joints may be affected later. The synovial membrane typically swells forming pulpy masses or fringes causing the joints to be enlarged. A gradual destruction of the articular cartilage finally results in complete disability and fusion of the joint surfaces. Customary symptoms include pain and swelling of the joints together with increasing stiffness and disability as the condition continues. The joints may eventually become distorted or deformed.

Another form of arthritis is osteoarthritis which is a degeneration of articular cartilage and bone, a degenerative condition.

For both forms of arthritis conventional therapy has included the use of corticosteroids, initially at a small dose and continued, often increased slowly, for a period of several years until the desired degree of control/mobility is attained. Prednisone is often used. For osteoarthritis an intra-articular injection of corticosteroids is often recommended for acute inflammations and episodes. Other treatments have included the administration of salicylates, notably aspirin, gold salts, ibuprofen, indomethacin, oxyphenbutazone and the like.

Among the advantages of the method of the present invention the patient is able to consume the required amount of bisulfite orally and without the danger of seroid therapy and its attendant risks, or the stomach upset and blood anormalities often associated with other products, such as indomethacin. The bisulfite itself is a safe, food-grade product well tolerated by virtually all patients.

In some of the clinical studies reported below there has been a complete remission of symptoms and therapy is stopped; in other patients therapy is maintained for longer periods of time and probably may be continued indefinitely.

Use of the present invention frequently leads to symptomatic and objective improvement in arthritic symptoms and conditions in man. By the term "symptomatic improvement", as used herein, reference is had to an improvement in subjective symptoms as reported by that patient. By the term "objective improvement", as used herein, reference is had to a measurable and objective change in the patient's condition.

In a second aspect of my invention I have discovered that sodium bisulfite, either as such or in an aqueous solution of sulfite ions (SO$_3$=), is useful in low doses and over certain periods in the treatment of the symptoms of epilepsy, particularly gran mal and petit mal, when administered to humans in a dilute aqueous solution.

Treatment of Epilepsy: A second emobodiment of the present invention is directed to the treatment of epilepsy and symptoms experienced by those afflicted with epileptic conditions. Epilepsy is an episodic disturbance of consciousness during which generalized convulsions may occur. The condition is of unknown etiology, but is often hereditary, and is manifested by symptoms of a peculiar sensation, smell or feeling, called an "aura" proceeding the loss of consciousness and often convulsions. Patients often complain of an initial noxious, foul smell, such as that of burning rubber. The patient is apt to fall during an attack, often injuring himself. He or she also may bite his tongue, become incontinent and awake to realize that something has happened only because of muscular soreness. Gran mal epilepsy is often preceded by an aura, beginning in a finger or toe and rising until the head is involved. The patient may give a shrill cry followed by unconsciousness. Tonic spasms are often followed by clonic spasms. Petit mal, another form of epilepsy, is evidenced by short seizures consisting of only momentary unconsciousness. See generally Goodman and Gilman, *The Pharmacological Basic of Therapeutics*, pp. 201–226 (1975), the disclosure of which is hereby incorporated by reference.

The term epilepsies is a collective designation for a group of chronic central nervous system disorders having in common brief episodes (seizures) associated with loss or disturbance of consciousness, usually but not always with characteristic body movements (convulsions) and sometimes autonomic hyperactivity, and always correlated with abnormal and excessive EKG disturbances. Epileptic seizures in an individual patient are classified on the basic of the clinical manifestations of the attacks and the EKG pattern.

Seizure types are often used to classify the particular type or types of epilepsy which include gran mal (generalized tonic-chronic), absence (petit mal), cortical focal, temporal lobe (psychomotor) and infantile that often occur in young children. In some of the clinical studies reported below there has been a complete remission of symptoms and therapy is stopped; in other patients therapy is maintained for longer periods of time.

Use of the present invention leads to symptomatic and objective improvement in epileptic conditions in man. By the term "symptomatic improvement", as used herein, reference is had to an improvement in subjective symptoms as reported by that patient. By the term "objective improvement", as used herein, reference is had to a measurable and objective change in the patient's condition.

Other and further aspects, objects, purposes, advantages, aims, utilities, features and the like will be apparent to those skilled in the art from a reading of the present application.

DETAILED DESCRIPTION OF THE INVENTION

More particularly, this invention concerns a process for treating a human suffering from the symptoms of arthritis wherein there is introduced a chemical agent comprising at least one compound which in aqueous solution furnishes at least one ion selected from the group consisting of bisulfite (which is preferred) and sulfite, the ion being present in a pharmaceutically effective amount of sodium bisulfite. Inorganic salts of sulfurous acid are suitable agents for practicing the invention, such as the pharmaceutically acceptable and existing compounds of the alkali metal, alkaline earth metal and ammonium salts of bisulfite and sulfites, including metabisulfites. Preferred are the sodium, potassium, calcium and magnesium salts.

In one preferred mode of using this invention, an aqueous solution of from about 1 to 15% by weight sodium bisulfite is prepared. Such solution is orally consumed by a human at the total (or accumulated) dose rate ranging from 0.2 to 4.0 mg per each kilogram of body weight per day, more preferably in the form of from two to four spaced doses per day, each such dose being preferably taken after meal time. A presently most preferred dose rate comprises one in the range from about 1.0 to 3.4 mg per kg. of body weight per day taken in the form of at least two spaced oral doses (using an aqueous solution as described herein).

In such mode of using this invention, one achieves symptomatic improvement in arthritic symptoms.

It is believed that larger or smaller doses may be used in accordance with the spirit and scope of the present invention. One dose rate, for example, considered effective is in the range of about 0.2 to 150 mg per day for an average human adult patient of approximately 70 kg. One knowledgeable in this art will select a regimen of therapy that provides subjective, symptomatic relief to the patient. Dose ranging studies in human volunteers indicate that single dose of up to 1,000 mg of sodium metabisulfite are tolerated without adverse effects.

The use of this invention is preferably practiced at present using a dilute aqueous solution of sodium bisulfite. Because of the tendency for sodium bisulfite to undergo oxidation when in aqueous solution and oxygen is present, it is presently common and even preferred in using this invention to employ a solution which comprises on a 100 percent by weight total solution basis:

(a) from about 1 to 15 percent by weight of dissolved inorganic solids, and (b) the balance up to 100 percent by weight of any given solution being water.

In such solution, such dissolved inorganic solids comprise on a calculated 100 percent by weight dry basis:

(a) at least about 50 and more preferably at least 90 percent by weight sodium bisulfite, and (b) the balance up to 100 percent by weight thereof being inorganic compounds produced or producible by the oxidation of sodium bisulfite.

The water used in such a solution is preferably purified (e.g. filtered, deionized, distilled or the like). After preparation, such a solution is preferably stored in a closed container to reduce oxidation.

Such an aqueous solution can be directly consumed by a patient as drops (e.g. from about 5 to 20 drops per meal, depending upon dose rate for an individual patient) or as a capsule or the like, as desired. A preferred dosage delivery system is a dropper bottle filled with an aqueous solution of sodium metabisulfite or a pharmaceutically acceptable compound capable of releasing $SO_3^=$ ions in an aqueous solution. Individual dosage units can range from about 50 to about 500 mg. each.

Symptomatic improvement in a patient's condition may occur within a few days to a few weeks of continuous usage of sodium bisulfite in accord with the teachings of this invention and as illustrated below.

One important advantage of the present invention is the circumstance that the indicated desirable results are achieved with surprisingly little or no apparent side effects.

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

PREPARATION OF THE SOLUTION

A sodium bisulfite is prepared by dissolving pharmaceutical grade (U.S.P. Grade) powdered sodium bisulfite (sodium metabisulfite) in distilled water at room temperature to form an eleven percent by weight aqueous solution.

This solution is then placed into a series of plastic squeeze bottles, each with a volumetric capacity of about 50–52 ml. Each bottle is provided with a cap permitting drop-wise dispensing of solution from such bottle at an estimated rate of 15 drops per ml. This is sometimes identified below as Agent C. In the studies reported below no other form of anti-arthritic therapy was used unless otherwise indicated.

In each of the following numbered case histories, each patient is provided with such a bottle of the above solution and is instructed to dose himself (or herself, as the case may be) from the bottle so provided at the rate indicated (in drops) to be taken orally at the frequency stated, preferably after each of his (her) three daily meals. When the contents of one such bottle is thus so gradually consumed by an individual patient, another is provided to him (her).

Treatment of Arthritis

EXAMPLE 1

A 28 year old woman, 55 kilograms body weight, temperature 37° C., blood pressure 120/70 was examined. Rheumatoid arthritis was diagnosed based on clinical study and immunological tests.

The patient's symptoms consisted of pains in the interfalangical articulations, both hands, as well as a discrete deformation on one hand. Previous treatment consisted of antirheumatics and Artilan suppositories, used normally in severe phases of this illness. At first there was a discrete improvement, followed by pain which increased in intensity using this conventional therapy. Sodium bisulfite solution (11%), as described above, was prescribed 10 drops per dose, twice daily. Approximately 10 days later there was a favorable improvement, pain disappeared and up to the present this patient continues with this same treatment with a 10 drops dose twice a day; the deformity has not progressed and patient is comfortable.

EXAMPLE 2

A woman, 38 years old, 70 kilograms body weight, 37° C., blood pressure 140/90 was diagnosed as having rheumatoid arthritis based on specific tests including the Rheumatoid factor and others. The pathological state started approximately four months prior to treatment with pain in the articulations of both hands; no deformity was observed. Intensity of the pain was of a moderate degree. This patient had also received an antirheumatic treatment. Previous therapy was stopped and the patient was given a solution of sodium metabisulfite, as described above, to be taken at a rate of one drop per every ten kilograms of body weight, i.e. 7 drops, three times a day.

The desired effect appeared approximately ten days after therapy with sodium metabisulfite was initiated. This patient reported having experienced some disagreeable slight manifestations, so the dose was diminished to 5 drops 3 times a day, and those slight manifestations disappeared as well as the pain in the articulations. This patient continues to be maintained with the prescribed dose.

EXAMPLE 3

A 58 year old man, 75 kilograms body weight, temperature 37° C., blood pressure 150/90. This patient began deforming rheumatoid arthritis approximately 20 years ago. The intense deformation was localized in both hands, accompanied with severe pains. Prednisone, analgesics and anti-inflammatories were prescribed unsuccessfully.

An 11% aqueous sodium metabisulfite solution was prescribed for the patient, 7 drops 3 times daily, and after 30 days therapy all the pains disappeared. This patient was followed for 2 years and continues to be free of pain; the joint deformation has not continued.

EXAMPLE 4

A 52 year old woman, 65 kilograms body weight, temperature 37° C., blood pressure 150/85 was diagnosed as having rheumatoid arthritis existing for approximately 7 years. She was treated by various doctors and the diagnosis was made with specific studies.

For a two month period of time this patient was given only Agent C, 6 drops 3 times daily. In only 8 days following initiation of therapy with the sodium bisulfite solution the patient was examined and the inflammation and pains in both hands diminished completely.

EXAMPLE 5

A 22 year old woman, 50 kilograms body weight, temperature 37° C., blood pressure 120/60 was examined and diagnosed as having rheumatoid arthritis (Juvenile). The patient was treated with gold salts and antirheumatics, with no favorable result.

This patient was given Agent C at a rate of 5 drops 3 times daily and observed after a period of approximately 3 months. The analgesic and anti-inflammatory effects of Agent C were very noticeable, the intensity has diminished considerably, as well as the inflammation. Therapy continues at the same rate.

EXAMPLE 6

A woman, age 76, 53 kg. weight, blood pressure 120/90, temperature 35.8°–36.2° C. was diagnosed as having arthritis as evidenced by deformation in the toes and fingers. Agent C was employed at a rate of 6 drops twice daily. Twenty days following initiation of therapy the patient reported that pains were diminished, and the patient appeared to be in better health. After about 4 months of therapy pains had disappeared completely; inflammation was still present but to a smaller degree.

This patient was followed for one year, maintained at the same dosage level of Agent C and continued to be free from pain with relatively no inflammation.

EXAMPLE 7

A woman, age 78, weight 56 kg., temperature 36.4° C., blood pressure 122/80, was examined and diagnosed as having arthritis. Symptoms included inflammation of the finger joints progressing over a 20 year period, with eventual difficulty in grasping objects in her hands. Therapy was initiated with Agent C, 5 drops 3 times a day. After approximately 15 days, pain in the finger joints subjectively ceased. Finger deformation was still present, even after extended period of therapy, although the fingers did not appear to have increased in size.

EXAMPLE 8

A woman, age 46, 68 kg., was diagnosed as having arthritis. Agent C was administered 7 drops twice daily and the patient observed. After one year's therapy the patient complained of no pains and inflammation was virtually completely gone.

Treatment of Epilepsy

EXAMPLE 9

A boy, 12 years in age, was diagnosed as having epilepsy (petit mal). Principal symptoms included an abrupt cessation of activity, a fixed glance or stare, eyes rolled upwardly, 3 ocular movements per second, deviation of the ocular globes and of the head, shaking of lips and hands, and urinary incontinence. Attacks occurred at a rate of about 3 to 5 every two weeks.

Therapy was initiated with an 11% aqueous solution of sodium bisulfite: 6 drops of the solution were added to a glass of water and the contents taken after meals, three times daily. Treatment continued and was observed on an approximate monthly basis with the following result.

| months following initial therapy | observation |
| --- | --- |
| 2 | no improvement |
| 3 | frequency of convulsions reduced |
| 5 | convulsive crises disappear |
| 6 | no convulsions |
| 7 | therapy was suspended |
| 9 | one crisis reported, lasted |

| months following initial therapy | observation |
| --- | --- |
| | 30 seconds, therapy resumed |
| 10 | no convulsions |
| 11 | therapy stopped |

Thirteen months following initial treatment, with therapy stopped for 2 months, the patient appeared well, free of convulsive crises and in an improved general state of health.

EXAMPLE 10

An 8 year old boy suffer from petit mal epilepsy exhibited the following symptoms: loss of consciousness for about 30 seconds, deviation of the ocular globes, tonic and clonic convulsions, incontinence of the bowel with cephalalgia lasting for 1-2 minutes. Attacks occurred at a rate of about 2 per month. Agent C was administered at a rate of 4 drops 3 times a day as in the previous example. The patient was observed periodically over one year's time; the clinician's observations were as follows:

| months following initial therapy | observation |
| --- | --- |
| 2 | no change in condition |
| 4 | one convulsive crisis per month; 30 seconds in duration |
| 5 | no convulsive crises |
| 6 | no crisis, treatment with Agent C suspended |
| 10 | no further evidence of convulsive crises |
| 12 | patient is asymptomatic and considered controlled |

EXAMPLE 11

A 3 year old boy suffered frequent tonic and clonic convulsions with fainting and cyanosis, heavy and noisy breathing, deviation of the ocular globes and head with urinary and fecal incontinence. The patient was diagnosed as suffering from petit mal epilepsy and 2 drops of Agent C 3 times a day were prescribed. Convulsions stopped 2 months following initiation of therapy. Agent C was discontinued 1 month later and the patient remained asymptomatic and free of convulsive crises 5 months following the date of initial treatment.

EXAMPLE 12

A 12 year old boy suffering from fainting lasting about 30 seconds, deviation of the ocular globes and head, salivation and tongue biting was diagnosed as having petit mal epilepsy. Attacks came at the rate of 3 to 4 per week and lasted about one minute. Agent C was prescribed, 6 drops 3 times a day. This treatment continued for 4 months until the frequency of the attacks was reduced to one every 2 weeks, however the intensity and the duration were the same.

| months following initial therapy | observation |
| --- | --- |
| 6 | one crisis occurred 20 seconds in duration |
| 8 | no convulsions |
| 9 | no convulsions |
| 12 | no convulsions |
| 14 | no convulsions, patient discontinued taking Agent C |

EXAMPLE 13

A 4 year old boy weighing 18 kg. diagnosed as having epilepsy (petit mal) was observed to suffer from a convulsive crisis, including deviation of the eyes and fainting lasting for about 30 seconds. Treatment with an 11% aqueous solution of sodium bisulfite was commenced at a rate of 3 drops 3 times a day, as in the previous examples. No substantial improvement in the patient's condition was noted until 4 months of therapy was completed when the crisis condition stopped. The patient discontinued taking the solution and after 5 months without therapy the patient was discharged from the clinician's care.

EXAMPLE 14

An 18 year old male weighing 58 kg, blood pressure 130/80 was diagnosed as having gran mal epilepsy. Symptoms included paralysis of the face muscles (cephalalgia), generalized convulsions followed by fainting, clonic and tonic movements with cyanosis and heavy, noisy breathing, tongue biting, general confusion and fatigue. Attacks occurred twice a month. Agent C was prescribed, 6 drops 3 times a day. Five months after initial treatment the patient continued to follow the prescribed therapy and remained free of convulsions and facial paralysis.

EXAMPLE 15

A 31 year old man, 70 kg in weight, blood pressure 140/80 suffering from intense cephalalgia, confusion and spontaneous mentally aberrant periods was diagnosed as having gran mal epilepsy. Attacks occurred about 1 every 2 weeks. Agent C, 7 drops 3 times daily as in Example 1, was prescribed. Therapy continued and after 4 months the patient reported he was free of convulsions and facial paralysis.

EXAMPLE 16

An 18 year old male, 48 kg, blood pressure 110/65 reported an aura followed by fainting with cyanosis. Tongue biting, tonic and clonic movements followed by heavy breathing, fatigue and general mental confusion followed. These attacks occurred twice a month and the patient was considered to suffer from gran mal epilepsy. Five drops of Agent C were prescribed to be taken orally 3 times a day, preferably after meals. Convulsive crises diminished over a period of time and 4 months following initial therapy the patient reported no convulsions or attacks.

EXAMPLE 17

An 18 year old woman, 48 kg, blood pressure 110/65 suffered from an aura, manifested by the apparent smell of a foul odor and paresthesis, followed by fainting with cyanosis. Tongue biting and tonic, clonic movements followed as well as heavy breathing and general mental confusion and fatigue. Attacks occurred at a rate of about 2 per month. Agent C at a rate of 5 drops 3 times a day was prescribed and after 3 months of treatment the patient reported no convulsions.

EXAMPLE 18

A sixteen year old boy weighing 50 kg suffered from weekly attacks including fainting with clonic and tonic contractions, tongue biting, interrupted breathing and both urinary and fecal incontinence was diagnosed as suffering from gran mal epilepsy. Five drops of Agent C were prescribed to be taken orally 3 times a day, as in Example 1. The frequency of the convulsions diminshed for several months until 6 after initial therapy the patient was free from convulsions. Eight months from initial treatment therapy was stopped and the patient remained free from convulsions or his other previous difficulties for a period of 14 months.

EXAMPLE 19

A 38 year old man, 72 kg, blood pressure 180/80, complained of typical gran mal symptoms including a bad odor aura, generalized convulsions with extensive rigidity of the body and extremities followed by clonic movements, temporary breathing interruptions, cyanosis and fainting. These symptoms happened about 4 times a month and each lasted about 4 minutes. Agent C was prescribed, 7 drops 3 times a day, and the results observed are as follows:

| months following initial therapy | observation |
| --- | --- |
| 2 | no symptoms or convulsions |
| 4 | no symptoms |
| 5 | no symptoms |
| 9 | therapy discontinued |
| 13 | a convulsion lasting 3 minutes was reported; therapy was resumed |
| 16 | therapy discontinued |
| 20 | no convulsions reported while continuing therapy with Agent C |

EXAMPLE 20

A 25 year old woman weighing 63 kg was diagnosed as having gran mal epilepsy. Her symptoms included an aura (manifested by a feeling of fear and paresthesia in the arms), generalized tonic and clonic convulsions lasting about 5 minutes with a frequency of six spells per month coincident with menstruation. Agent C was prescribed, 7 drops 3 times a day (one drop per kg of body weight) and the results observed are as follows:

| months following initial therapy | observation |
| --- | --- |
| 1 | convulsions continue, no change in condition |
| 2 | no change in condition |
| 3 | no change in condition |
| 5 | crises diminish in frequency and intensity; 3 per month each lasting 1-2 minutes |
| 7 | continued decline in condition |
| 9 | no symptoms or signs of epilepsy |
| 11 | one convulsive crisis lasting 1 minute |
| 12 | no symptoms |
| 13 | no symptoms |
| 18 | two crises each lasting 1 minute |
| 20 | no symptoms |
| 23 | no symptoms |
| 26 | no symptoms, therapy discontinued |
| 38 | no symptoms or signs of epilepsy reported |

The patient remained free from convulsion crises and the like for at least one year after therapy was discontinued.

EXAMPLE 21

A 26 year old man, 68 kg, blood pressure 118/70 was diagnosed as having epilepsy (gran mal). Symptoms included an initial aura (visual and auditory hallucinations), generalized convulsions, urinary incontinence, tongue biting, deviation of the ocular globes, cyanosis, difficulty in breathing and other characteristic symptoms. Attacks occurred 3–4 per week and each lasted about 3–4 minutes. Agent C was prescribed, 7 drops 3 times a day preferably after meals, as in Example 1. Observations are as follows:

| months following initial therapy | observation |
| --- | --- |
| 1 | no change in condition |
| 2 | no change in condition |
| 3 | crises diminished in frequency and duration to 2 minutes each |
| 5 | one crisis lasting 3–4 minutes reported |
| 7–20 | no crises |

Therapy with Agent C was suspended 2½ years after initial treatment. The patient continued to be asymptomatic for 6 months thereafter.

EXAMPLE 22

A 4 year old boy, 22 kg in weight, was diagnosed as having epilepsy. Principal signs and symptoms included aura (manifested by the sensation of fear), followed by generalized convulsions and faintness, extensory rigidity, tonic at the trunk and extremities followed by clonic movements, cyanosis and noisy breathing. The frequency was about 3 attacks per month each lasting about 2-3 minutes. Agent C was prescribed at twice the usual dose, 5 drops of the 11% aqueous solution taken 3 times a day. Symptoms stopped after 3 months of therapy. This young patient tolerated the dosage well and all symptoms have disappeared.

EXAMPLE 23

A 30 year old man, 68 kg, blood pressure 138/70 was diagnosed as having epilepsy with the usual symptoms and signs. Attacks would happen about 5 per month each lasting about 4 minutes. Agent C was prescribed at an elevated dose of 9 drops 3 times a day. Symptoms were gone after only one month of treatment and the patient was maintained for at least 7 months thereafter without crisis.

EXAMPLE 24

A 12 year old boy, 35 kg, exhibited signs of fainting lasting 30 seconds with the sensation of clumsiness, a fixed glare with slight movement of the lips and hands. These events would happen as many as 6 times per week but last only about 30 seconds each. The patient was considered to have epilepsy and was prescribed 5 drops of Agent C (an elevated dosage) three times a day. After about one month the symptoms disappeared and the patient remained asymptomatic for at least 5 months.

What is claimed is:

1. A method of treating epilepsy and epileptic conditions in a person suffering from the symptoms of epilepsy comprising orally administering to said person a symptom-alleviating amount of a compound which in aqueous solution furnishes sulfite ions, bisulfite ions or both sulfite and bisulfite ions.

2. The method of claim 1 in which the compound is selected from the group consisting of alkali metals, alkaline earth metals and ammonium sulfites and bisulfites, and alkali metal bisulfites at an effective rate of from about 0.2 to about 50 mg. thereof per kilogram of body weight per 24 hours.

3. The method of claim 2 in which the compound is a sodium, potassium, calcium or magnesium salt.

4. The method of claim 3 in which the compound is sodium bisulfite.

5. The method of claim 3 in which the compound is sodium metabisulfite.

6. The method of claim 1 in which the person is suffering from gran mal epilepsy.

7. The method of claim 1 in which the person is suffering from petit mal epilepsy.

* * * * *